| United States Patent [19] | [11] Patent Number: 4,639,445 |
|---|---|
| McQuinn et al. | [45] Date of Patent: Jan. 27, 1987 |

[54] METABOLITES OF TRIAZOLO[1,5-C]PYRIMIDINES

[75] Inventors: Roy L. McQuinn, White Bear; James J. Wade, Oakdale, both of Minn.

[73] Assignee: Riker Laboratories, St. Paul, Minn.

[21] Appl. No.: 791,594

[22] Filed: Oct. 25, 1985

[51] Int. Cl.$^4$ .................... C07D 417/04; A61K 31/54
[52] U.S. Cl. .................................. 514/222; 544/58.2
[58] Field of Search ....................... 544/58.2; 514/222

[56] References Cited

FOREIGN PATENT DOCUMENTS

| 1205144 | 1/1960 | France. |
| 859287 | 1/1961 | United Kingdom. |
| 873223 | 7/1961 | United Kingdom. |
| 897870 | 5/1962 | United Kingdom. |

OTHER PUBLICATIONS

G. W. Miller, et al., J. Chem. Soc., (1965), pp. 3357–3368.

*Primary Examiner*—John M. Ford
*Attorney, Agent, or Firm*—Donald M. Sell; James A. Smith; Robert W. Sprague

[57] ABSTRACT

The present invention relates to metabolites of 2,5-diethyl-7-(4-thiomorpholino)-1,2,4-triazolo[1,5-c]-pyrimidine which are active as bronchodilators.

7 Claims, No Drawings

METABOLITES OF TRIAZOLO[1,5-C]PYRIMIDINES

The present invention relates to metabolites of certain triazolo[1,5-c]pyrimidines, and more specifically to metabolites of 2,5-diethyl-7-(4-thiomorpholino)-1,2,4-triazolo[1,5-c]pyrimidine. The pharmacological use of the compounds of the invention as bronchodilators and pharmaceutical compositions comprising the compounds are also within the scope of the invention.

Some 1,2,4-triazolo[1,5-c]pyrimidines are known to the art. Certain 1,2,4-triazolo[1,5-c]pyrimidines are disclosed as being bronchodilators in the patents discussed below, the compounds being referred to therein as triazolo[2,3-c]pyrimidines:

United Kingdom Pat. No. 859,287 discloses 2-amino-1,2,4-triazolo[1,5-c]pyrimidines which are substituted on the pyrimidine ring at the 5, 7 and 8 positions by certain combinations of substituents selected from hydrogen, alkyl, halogen-substituted alkyl, hydroxy-substituted alkyl, alkoxy-substituted alkyl, alkenyl, cycloalkyl, amino, alkylamino, dialkylamino, phenyl, alkylthio, alkoxy and halogen substituents.

United Kingdom Pat. No. 873,223 discloses 2-amino or 2-acetamido-1,2,4-triazolo[1,5-c]pyrimidines which are substituted on the pyrimidine ring at the 5, 7 and 8 positions by certain combinations of substituents selected from hydrogen, alkyl, halogen-substituted alkyl, alkoxy-substituted alkyl, alkenyl, cycloalkyl, alkylthio and halogen substituents.

United Kingdom Pat. No. 897,870 discloses 2-alkylamino-1,2,4-triazolo[1,5-c]pyrimidines, 2-dialkylamino-1,2,4-triazolo[1,5-c]pyrimidines, and 1,2,4-triazolo[1,5-c]pyrimidines containing a piperidino or morpholino substituent bonded at the 2-position through the nitrogen atom, which compounds are substituted on the pyrimidine ring at the 5, 7 and 8 positions by certain combinations of substituents selected from hydrogen, alkyl, halogen-substituted alkyl, hydroxy-substituted alkyl, alkenyl and halogen substituents.

The following article discloses the synthesis of certain 1,2,4-triazolo[1,5-c]pyrimidines as potential bronchodilators:

G. W. Miller et al., *J. Chem. Soc.*, 1963, 3357, discloses 1,2,4-triazolo[1,5-c]pyrimidines (referred to therein as triazolo[2,3-c]pyrimidines) which are substituted at the 2-position by hydroxy, halogen, alkoxy, amino or substituted amino substituents and on the pyrimidine ring by alkyl substituents, or alkyl and halogen-substituted alkyl substituents.

Still other 1,2,4-triazolo[1,5-c]pyrimidines are disclosed in the following patent.

French Pat. No. 1,205,444 discloses compounds which are purportedly 7-methyl-1,2,4-triazolo[4,3-c]pyrimidines having, for example, an amino or heterocyclic amino substituent in the 5-position. However, it is known that the compounds actually obtained when the examples are followed are the corresponding 7-methyl-1,2,4-triazolo[1,5-c]pyrimidines.

Finally, the following patent and applications which are owned by the assignee of the instant application relate to triazolopyrimidines which are bronchodilators.

European Patent Application No. 84301383.0 (published on Sept. 10, 1984 as 0 121 341) describes various triazolo[1,5-c]pyrimidines including 2,5-diethyl-7-(4-thiomorpholino)-1,2,4-triazolo[1,5-c]pyrimidine of which the instantly claimed compounds are metabolites.

Copending U.S. patent application Ser. No. 583,386, filed Feb. 24, 1984, describes 2,5-diethyl-7-[4-(1-oxothiomorpholino)]-1,2,4-triazolo[1,5-c]pyrimidine and 2,5-diethyl-7-[4-(1,1-dioxothiomorpholino)]-1,2,4-triazolo[1,5-c]pyrimidine.

The present invention relates to 1,2,4-triazolo[1,5-c]pyrimidines which are bronchodilators. The invention also relates to a method for inducing bronchodilation in a mammal using a 1,2,4-triazolo[1,5-c]pyrimidine of the invention, and to pharmaceutical compositions comprising an effective amount of a 1,2,4-triazolo[1,5-c]pyrimidine of the invention and a pharmaceutically acceptable carrier.

Specifically, the present invention relates to compounds of the Formula I

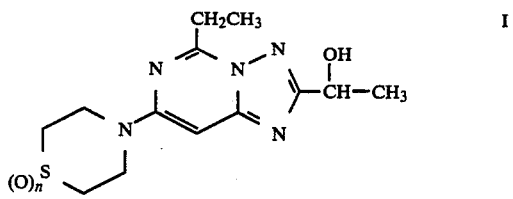

wherein n is 1 or 2; and pharmaceutically acceptable acid-addition salts thereof.

The compound of Formula I wherein n is 1 is named 5-ethyl-2-(1-hydroxyethyl)-7-[4-(1-oxothiomorpholino)]-1,2,4-triazolo[1,5-c]pyrimidine, and the compound of Formula I wherein n is 2 is named 5-ethyl-2-(1-hydroxyethyl)-7-[4-(1,1-dioxothiomorpholino)]-1,2,4-triazolo[1,5-c]pyrimidine.

The carbon atom substituted by the hydroxyl moiety is asymmetric in the compounds of the invention. Both compounds have been determined to be levorotatory, the specific rotations in ethanol being $[\alpha]_D^{28} = -20.6$ for 5-ethyl-2-(1-hydroxyethyl)-7-[4-(1-oxothiomorpholino)]-1,2,4-triazolo[1,5-c]pyrimidine and $[\alpha]_D^{27} = -18.2$ for 5-ethyl-2-(1-hydroxyethyl)-7-[4-(1,1-dioxothiomorpholino)]-1,2,4-triazolo[1,5-c]pyrimidine. It is understood that the specific rotation will depend upon a variety of factors including purity of the compound.

The bronchodilator activity of the compounds of Formula I was assessed by the measurement of effects on isolated tracheal spirals. This is a well-known and long established in vitro test method. The bronchodilator activity was determined according to the following procedure: Female guinea pigs were sacrificed and each trachea removed and cut into a spiral strip. This strip was mounted in a constant temperature (37° C.) muscle bath having a volume of approximately 15 ml. The bathing medium was Krebs-Henseleit solution. Movement of the tracheal strip was measured by means of an isometric transducer connected to an electric recorder. The bath was aerated with a mixture of 95% carbon dioxide and 5% oxygen. Contractions were induced in the strips by the addition of histamine, acetylcholine or barium chloride in an amount of 0.4, 0.5 or 250 micrograms per ml, respectively. The amount of a given compound of Formula I (measured in micrograms per ml) required to provide greater than 75% relaxation of drug-induced contraction is considered an effective concentration. For comparison, a well known standard bronchodilator, aminophylline, requires concentrations of 50 micrograms per ml versus histamine, 100 micrograms per ml versus acetylcholine and 10 micrograms per ml versus barium chloride to provide greater than 75% relaxation.

Both of the compounds of Formula I were active in the in vitro test, and could be tested in vivo in the guinea pig for oral activity in the so-called histamine aerosol method described in U.S. Pat. No. 3,248,292, incorporated herein by reference. This test is modified slightly in that a 0.1% aqueous solution of histamine is used as the agent for inducing bronchial constriction. Oral doses are measured in mg/kg of body weight of the guinea pig.

The compounds of Formula I may be administered to mammals in order to obtain bronchodilation. The compounds may be administered orally, parenterally or by inhalation. Preferably they are administered orally in tablets or capsules. The estimated effective human dose will be in the range of 0.1 to 5 mg/kg of body weight.

Salts of compounds of Formula I are generally prepared by reaction with an equimolar amount of a relatively strong acid, preferably an inorganic acid such as hydrochloric, sulfuric or phosphoric acid, in a polar solvent. Isolation of the salt is facilitated by the addition of a solvent in which the salt is insoluble. An example of such a solvent is diethyl ether.

The compounds of Formula I, either as the free base or in the form of a pharmaceutically acceptable acid-addition salt, can be combined with conventional pharmaceutical diluents and carriers to form such dosage forms as tablets, capsules, suspension, solutions, suppositories and the like.

The pharmaceutical carrier employed may be, for example, either a solid or liquid. Examples of solid carriers are lactose, terra alba, sucrose, talc, gelatin, agar, pectin, acacia, magnesium stearate, stearic acid, and the like. Liquid carriers include syrup, peanut oil, olive oil, water and the like. Similarly, the carrier or diluent can include a time delay material well known to the art, such as glyceryl monostearate or glyceryl distearate, these being employed alone or, for example, in combination with a wax.

The compounds of Formula I are obtained by administering the bronchodilator compound 2,5-diethyl-7-(4-thiomorpholino)-1,2,4-triazolo[1,5-c]pyrimidine to a mammal, collecting urine from the mammal and separating the compounds of Formula I from the urine. The compound 2,5-diethyl-7-(4-thiomorpholino)-1,2,4-triazolo[1,5-c]pyrimidine may be prepared as described in copending application U.S. Ser. No. 471,836, filed Mar. 3, 1983, and commonly assigned.

Suitable laboratory mammals from which the metabolites may likely be obtained are dogs and rats.

Standard methods may be used for the separation of the metabolites from urine such as extraction, chromatography, precipitation and the like. The specific procedure utilized in the present invention was to extract the urine of a dog to which the compound 2,5-diethyl-7-(4-thiomorpholino)-1,2,4-triazolo[1,5-c]pyrimidine had been administered. Chloroform was used as the extraction solvent. The organic extracts were evaporated to provide a solid which was flash chromatographed on silica gel to provide separation of the two metabolites. Recrystallization followed by spectral analysis (i.e., nuclear magnetic resonance spectrometry, infrared spectrometry, or mass spectrometry), elemental analysis and comparison to known compounds of similar structure established the structures of the compounds of Formula I.

Pharmacological evaluation of the metabolites isolated as described herein demonstrated that both metabolites were quite active as bronchodilators in both in vitro and in vivo models.

The metabolites of Formula I are also quite useful for studying the metabolism of the parent compound, 2,5-diethyl-7-(4-thiomorpholino)-1,2,4-triazolo[1,5-c]pyrimidine.

Although it has not been established experimentally, it is presumed that the compounds of Formula I would also be metabolites of the compounds 2,5-diethyl-7-[4-(1-oxothiomorpholino)]-1,2,4-triazolo[1,5-c]pyrimidine and 2,5-diethyl-7-[4-(1,1-dioxothiomorpholino)]-1,2,4-triazolo[1,5-c]pyrimidine.

The following examples are provided to illustrate the methods used in the invention. They are not intended to limit the invention.

EXAMPLE 1

A dosage formulation was prepared containing 35.7% by weight of 2,5-diethyl-7-(4-thiomorpholino)-1,2,4-triazolo[1,5-c]pyrimidine granulated with lactose. This formulation was weighed into gelatin capsules, which were used to dose each of two beagle dogs at a rate of 51 mg/kg/day of the drug, split into two doses per day, for a two-day period. Dog (A) (12.6 kg) was dosed 4 times with 900 mg per dose of the formulation of 2,5-diethyl-7-(4-thiomorpholino)-1,2,4-triazolo[1,5-c]pyrimidine for a total dose of 1.29 g. Dog (B) (14.4 kg) was dosed 4 times with 1030 mg per dose of the formulation and received a total dose of 1.47 g. Urine was collected from both dogs from the time of first dosing to 19 hours after the final dose.

Total volumes of urine collected were 450 ml (Dog A) and 457 ml (Dog B). About 225 ml of urine was put on each of four extraction columns, (Extube ™, Analytichem International, Harbor City, Calif.) which were disposable extraction columns, capacity 300 ml. The columns were eluted first with three 200 ml portions of diethyl ether, then with eight 200 ml portions of chloroform. The ether fractions were discarded. Chloroform fractions of 400 ml were collected and combined with the same fraction from the other columns. Evaporation of the first three chloroform fractions provided a solid residue which was combined to provide 1.88 g of off-white solid.

The off-white solid was placed on a one-liter flash chromatography column, and eluted first with two liters of 1:9 ethanol:dichloromethane and then with two liters of 15:85 ethanol:dichloromethane. The first 150 ml of eluate was combined and evaporated to provide 0.96 g of white solid (designated hereinafter as C). The next 1275 ml of eluate was discarded. The next 1750 ml of eluate was combined and evaporated to provide 0.85 g of white solid (designated hereinafter as D).

Solid C was recrystallized with treatment with decolorizing charcoal from a mixture of 75 ml of ethyl acetate and 25 ml of hexanes. After cooling, the solid was separated by filtration, washed with hexanes and dried to give 0.69 g of white fluffy needles, m.p. 168°–169° C. Infrared, nuclear magnetic resonance and mass spectral analyses indicated the structure of the compound to be 5-ethyl-2-(1-hydroxyethyl)-7-[4-(1,1-dioxothiomorpholino)]-1,2,4-triazolo[1,5-c]pyrimidine. Analysis: Calculated for $C_{13}H_{19}N_5O_3S$: % C, 48.0; % H, 5.9; % N, 21.5; Found: % C, 47.6; % H, 5.9; % N, 21.3.

Solid D was recrystallized with treatment with decolorizing charcoal from a mixture of 50 ml of dichloromethane and 15 ml of hexanes. After cooling, the solid was separated by filtration, washed with hexanes and dried to provide 0.46 g of fluffy off-white solid, m.p. 192°–193° C. Infrared, nuclear magnetic resonance and mass spectral analyses indicated the structure of the compound to be 5-ethyl-2-(1-hydroxyethyl)-7-[4-(1-oxothiomorpholino)]-1,2,4-triazolo[1,5-c]pyrimidine. Analysis: Calculated for $C_{13}H_{19}N_5O_2S$: % C, 50.5; % H, 6.2; % N, 22.6; Found: % C, 50.4; % H, 6.1; % N, 22.8.

EXAMPLE 2

A solution of each of the compounds 5-ethyl-2-(1-hydroxyethyl)-7-[4-(1,1-dioxothiomorpholino)]-1,2,4-triazolo[1,5-c]pyrimidine (C) and 5-ethyl-2-(1-hydroxyethyl-7-[4-(1-oxothiomorpholino)]-1,2,4-triazolo[1,5-c]pyrimidine (D) in 0.1N hydrochloric acid was prepared by gentle heating.

Each of these solutions was diluted to provide various concentrations of the compound and the bronchodilator activity was measured by its effect in the isolated tracheal spiral model described hereinabove. The activity is shown below:

TABLE I

| Compound of the Invention | Agonist Employed | Percent Relaxation of Contraction at Indicated Concentration of Compound of the Invention (μg/ml) | | | | | |
|---|---|---|---|---|---|---|---|
| | | 1.25 | 2.5 | 5 | 10 | 25 | 50 |
| Compound D | Histamine | 55% | 80% | 85% | 100% | — | — |
| | Acetylcholine | 5% | 15% | 30% | 100% | — | — |
| | Barium chloride | 25% | 40% | 70% | 100% | — | — |
| Compound C | Histamine | — | 80% | 100% | — | — | — |
| | Acetylcholine | — | — | 25% | 15% | 55% | 60% |

TABLE I-continued

| Compound of the Invention | Agonist Employed | Percent Relaxation of Contraction at Indicated Concentration of Compound of the Invention (μg/ml) | | | | | |
|---|---|---|---|---|---|---|---|
| | | 1.25 | 2.5 | 5 | 10 | 25 | 50 |
| | Barium chloride | — | — | 40% | 60% | 50% | 85% |

What is claimed is:

1. A compound of the formula:

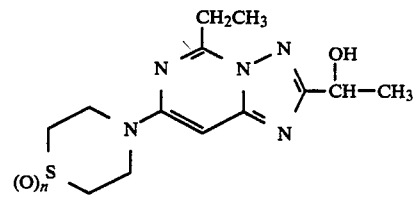

wherein n is 1 or 2; said compound being levorotatory; or a pharmaceutically acceptable acid-addition salt thereof.

2. A compound according to claim 1, wherein n is one.

3. A compound according to claim 1, wherein n is two.

4. A compound according to claim 1 in substantially pure form.

5. A bronchodilator pharmaceutical composition comprising a compound according to claim 1 and a pharmaceutically acceptable vehicle, said compound being present in an amount effective to obtain bronchodilation.

6. A method for obtaining bronchodilation in a mammal, comprising administering a compound according to claim 1 to said mammal in an amount effective to obtain bronchodilation.

7. A method according to claim 6, wherein the compound is administered orally.

* * * * *